United States Patent [19]

Abbott

[11] Patent Number: Plant 6,335

[45] Date of Patent: Oct. 11, 1988

[54] CHRYSANTHEMUM PLANT NAMED SATIN PINK GIN

[75] Inventor: Jesse D. S. Abbott, Chichester, England

[73] Assignees: Swallowfield Horticultural Enterprises Ltd; Framptons Nurseries Ltd, both of England

[21] Appl. No.: 932,792

[22] Filed: Nov. 20, 1986

[51] Int. Cl.[4] ..... A01H 5/00

[52] U.S. Cl. ..... Plt./80

[58] Field of Search ..... Plt./80

*Primary Examiner*—James R. Feyrer

*Attorney, Agent, or Firm*—Schwartz, Jeffery, Schwaab, Mack, Blumenthal & Evans

[57] ABSTRACT

A chrysanthemum plant named Satin Pink Gin particularly characterized by its decorative type inflorescence, generally flat inflorescence form with incurved petals, pink flower color, tall plant height, upright branching pattern, 10 week flowering response period, good shipping durability, and by its high grade cut.

1 Drawing Sheet

The present invention comprises a new and distinct cultivar of *Chrysanthemum morifolium*, Ramat., hereinafter referred to by the cultivar name Satin Pink Gin.

Satin Pink Gin is a naturally occurring sport of the parent cultivar Pink Gin and was discovered on May 30, 1984 by applicant as a single plant flowering in a block of the parent cultivar Pink Gin in a controlled environment in Titchfield, Hampshire, England. The new cultivar was noted by virtue of its pale pastel pink ray floret color, a color not available from previous selections of the cultivar Pink Gin.

Pink Gin, the parental cultivar of Satin Pink Gin, was originated from a hybridization made in a controlled breeding program in Chichester, West Sussex, England in 1970. The female parent of Pink Gin was the well-known cultivar Bluechip, a pink decorative spray cultivar bred by Yoder Brothers, Inc., Barberton, Ohio. The male parent of Pink Gin was Arctic, a creamy white decorative spray bred by Framptons Nurseries Ltd., Chichester, West Sussex, England. Pink Gin was discovered and selected as one flowering plant within the progeny of the stated parentage by Barry J. Machin on June 22, 1971 in a controlled environment in Chichester, West Sussex, England.

The first act of asexual reproduction of the new cultivar Satin Pink Gin was accomplished when vegetative cuttings were taken from the initial selection on July 10, 1984 in a controlled environment in Titchfield, Hampshire, England by a technician working under formulations established and supervised by applicant. Horticultural examination of selected units initiated Feb. 29, 1984 has demonstrated that the combination of characteristics as herein disclosed for Satin Pink Gin are firmly fixed and are retained through successive generations of asexual reproduction.

Satin Pink Gin has not been observed under all possible environmental conditions. The phenotype may vary significantly with variations in environment such as temperature, light intensity, and day length. The following observations, measurements and comparisons describe plants grown in Titchfield, Hampshire, England under greenhouse conditions which approximate those generally used in commercial practice, and specifically noted in Chart A attached to the present specification.

Of the many commercial cultivars known to the present inventor, the most similar in comparison to Satin Pink Gin is the parent cultivar Pink Gin. Reference is made to attached Chart B which compares certain characteristics of Satin Pink Gin to those same characteristics of Pink Gin. In comparison to Pink Gin, Satin Pink Gin has different inflorescence color and slightly more incurving petals. The diameter across the face of the inflorescence, plant height, branching pattern, flowering response period, inflorescence form and inflorescence type of Satin Pink Gin are similar to those same characteristics of Pink Gin.

The accompanying photographic drawing shows in a front view the typical inflorescence and foliage characteristics of Satin Pink Gin, with colors being as nearly true as possible with illustrations of this type.

In the following description, color references are made to The Royal Horticultural Society Colour Chart. The color values were determined between 4:00 to 4:30 p.m. on Sept. 24, 1986 under 200 foot candles of light intensity at Titchfield, Hampshire, England.

Classification:

*Botanical.*—*Chrysanthemum morifolium*, Ramat., cv. Satin Pink Gin.

*Commercial.*—Cut flower decorative spray.

INFLORESCENCE

A. Capitulum:

*Form.*—Flat.

*Type.*—Decorative spray.

*Diameter across face.*—3.25 inches (each lateral flower).

B. Corolla of ray florets:

*Color (general tonality from a distance of three meters).*—Shell pink.

*Color (upper surface).*—69A.

*Color (under surface).*—75D.

C. Corolla of disc florets: Almost no disc florets.

D. Reproductive organs:

*Androecium.*—Present in the one or two disc florets, scant pollen.

*Gynoecium.*—Present in both ray and disc florets, inferior bicarpeltate ovary, single style, 2 lobed stigma.

PLANT

A. General appearance:

*Height.*—Upright, tall height.

B. Foliage:

*Color (upper surface).*—137B.

*Color (under surface).*—137D.

*Shape.*—Spatulate, deeply lobed.

CHART A.

AVERAGE GREENHOUSE CHRYSANTHEMUM ENVIRONMENTS USED FOR TITCHFIELD, ENGLAND

| | Temperature used | | | |
|---|---|---|---|---|
| Season | Night | Bright Day | Cloudy Day | Lighting used |
| Autumn | 55 to 65 | 65 to 75 | 60 to 70 | 2–4 weeks at 4 hrs per night 7–10 fc |
| Winter | 60 to 65 | 65 to 75 | 60 to 70 | 4–5 weeks at 5 hrs per night 7–10 fc |
| Spring | 60 to 65 | 65 to 75 | 60 to 70 | 2–3 weeks at 4 hrs per night 7–10 fc |
| Summer | 55 to 75 | 70 to 90 | 65 to 75 | 2 weeks at 3 hrs per night 7–10 fc |

| Season | Black Cloth used | Supp $CO_2$ |
|---|---|---|
| Autumn | To 15 Sept on 6 pm off 7 am | From 15 Oct to 15 Mar up to 1000 vpm |
| Winter | None | From 15 Oct to 15 Mar up to 1000 vpm |
| Spring | From 15 March on 6 pm off 7 am | From 15 Oct to 15 Mar up to 1000 vpm |

CHART A.-continued

AVERAGE GREENHOUSE CHRYSANTHEMUM ENVIRONMENTS USED FOR TITCHFIELD, ENGLAND

| | | |
|---|---|---|
| Summer | From 15 March on 6 pm off 7 am | None |

CHART B.

COMPARISON OF SATIN PINK GIN AND PINK GIN

| Cultivar | Inflorescence Colour | Petal Shape | Diameter across face of inflorescence | Plant height |
|---|---|---|---|---|
| Satin Pink Gin | Shell pink | Very slightly incurved | 3.25 inches | Tall |
| Pink Gin | Pink | Flat | 3.25 inches | Tall |

| Cultivar | Branching pattern | Flowering response period | Inflorescence form and type |
|---|---|---|---|
| Satin Pink Gin | Upright | 10 week | Flat decorative spray |
| Pink Gin | Upright | 10 week | Flat decorative spray |

I claim:

1. A new and distinct cultivar of chrysanthemum plant named Satin Pink Gin, as described and illustrated, and particularly characterized by its decorative type inflorescence, generally flat inflorescence form with incurved petals, pink flower color, tall plant height, upright branching pattern, 10 week flowering response period, good shipping durability, and high grade cut.

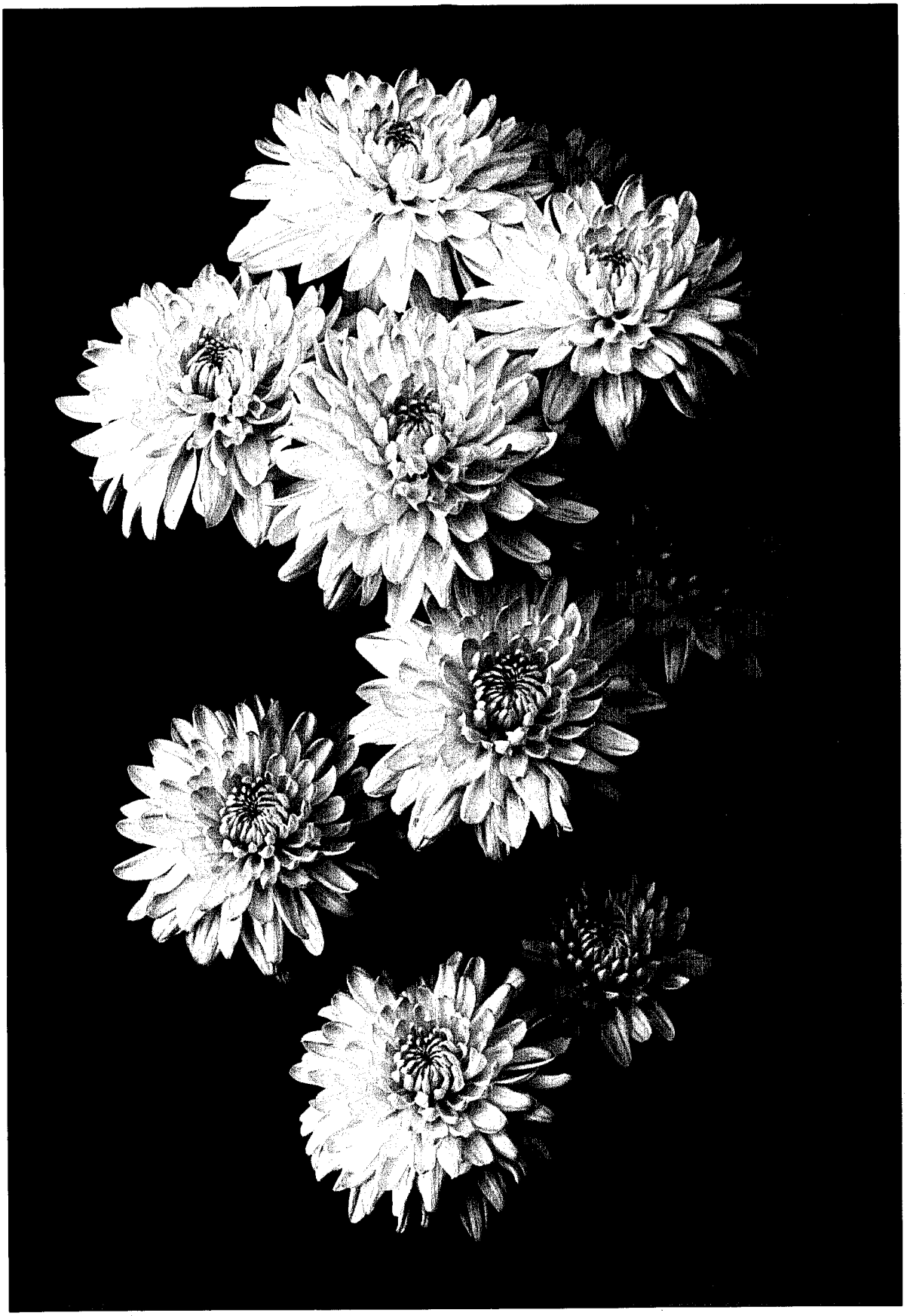

* * * * *